US007020288B1

(12) United States Patent
Ohashi

(10) Patent No.: US 7,020,288 B1
(45) Date of Patent: Mar. 28, 2006

(54) NOISE REDUCTION APPARATUS

(75) Inventor: Toshihiko Ohashi, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 436 days.

(21) Appl. No.: 09/807,706

(22) PCT Filed: Aug. 17, 2000

(86) PCT No.: PCT/JP00/05490

§ 371 (c)(1),
(2), (4) Date: Jul. 9, 2001

(87) PCT Pub. No.: WO01/15137

PCT Pub. Date: Mar. 1, 2001

(30) Foreign Application Priority Data

Aug. 20, 1999 (JP) ................................ 11/233819

(51) Int. Cl.
*A61F 11/06* (2006.01)
*G10K 11/16* (2006.01)
*H03B 29/00* (2006.01)

(52) U.S. Cl. .................................... 381/71.4; 381/71.8

(58) Field of Classification Search ............... 381/71.4, 381/71.1, 71.8, 71.2, 71.12, 71.7
See application file for complete search history.

(56) References Cited

U.S. PATENT DOCUMENTS 5,384,853 A * 1/1995 Kinoshita et al. ........ 381/71.12
5,416,846 A * 5/1995 Tamura et al. ............ 381/71.8
5,491,446 A 2/1996 Okada et al.
5,651,072 A * 7/1997 Nakao et al. .............. 381/71.2
5,748,748 A * 5/1998 Fischer et al. ............ 381/71.4

FOREIGN PATENT DOCUMENTS

| | | |
|---|---|---|
| EP | 0 461 801 | 12/1991 |
| JP | 3-50998 | 3/1991 |
| JP | 3-70490 | 7/1991 |
| JP | 5-11771 | 1/1993 |
| JP | 7-92988 | 4/1995 |
| JP | 7-210175 | 8/1995 |
| JP | 8-248963 | 9/1996 |
| JP | 8-314472 | 11/1996 |
| JP | 9-36784 | 2/1997 |
| JP | 11-166594 | 6/1999 |
| WO | 90/09655 | 8/1990 |

OTHER PUBLICATIONS

International Search Report corresponding to application No. PCT/JP00/05490.
English translation of PCT/ISA/220.
European Search Report, application No. 00953451.2, dated Apr. 11, 2002.

* cited by examiner

*Primary Examiner*—Ping Lee
(74) *Attorney, Agent, or Firm*—RatnerPrestia

(57) ABSTRACT

An active noise control system includes a source unit for generating regenerative signals, an ANC unit for processing signals so as to actively cancel noise, sensors for detecting the information on the inside and outside of a vehicle, a vehicle interior voice discriminating unit for discriminating voice of conversation generated in the vehicle interior, an amplifier for amplifying the signals processed by ANC unit and reproducing transducers for reproducing the signals amplified by the amplifier.

6 Claims, 6 Drawing Sheets

NOISE REDUCTION APPARATUS

This application is a U.S. National Phase Application of PCT International Application PCT/JP00/05490.

The present invention relates to a system for reducing noise in the interior of a vehicle such as a car.

FIELD OF THE INVENTION

In recent years, improvement in hardware performance, cost reduction, and the like are putting active noise control techniques into practical use. In particular, their effectiveness has been validated in noises in a low-frequency band that are difficult to be reduced by conventional passive measures. Such active techniques are mainly applied to the low-frequency band.

However, as for the application to noises in medium- and high-frequency bands, the application of such techniques to a noise elimination system for a vehicle interior was not easy because of the following two reasons: the long distances from the controlled sound sources to the hearing points tend to generate error and make control more difficult; and the acoustic space to be controlled is three-dimensional and thus has a plurality of hearing points. Moreover, extending frequency bands to be controlled to medium- and high-frequency bands posed a problem that even the conversation of passengers was eliminated because it was also a disturbance for the reproducing system.

DISCLOSURE OF THE INVENTION

It is an object of the present invention to correct these conventional defects and to provide a noise control system for reducing noises extending to medium- and high-frequency bands in the interior of a vehicle.

In order to address these problems, the active noise control system of the present invention comprises; a source unit for generating regenerative signals, an active noise control (ANC) unit for processing signals so as to actively cancel noise, sensors for detecting the information on the inside and outside of a vehicle; a vehicle interior voice discriminating unit for discriminating voices emanated in the vehicle interior, an amplifier for amplifying the signals processed by the ANC unit, and reproducing transducers for reproducing the signals amplified by the amplifier.

This structure allows reduction of noises extending to medium- and high-frequency bands in the interior of a vehicle.

PREFERRED EMBODIMENT OF THE INVENTION

Exemplary Embodiment

An exemplary embodiment of the present invention is hereinafter demonstrated with reference to FIGS. 1 through 13.

Figure 1:
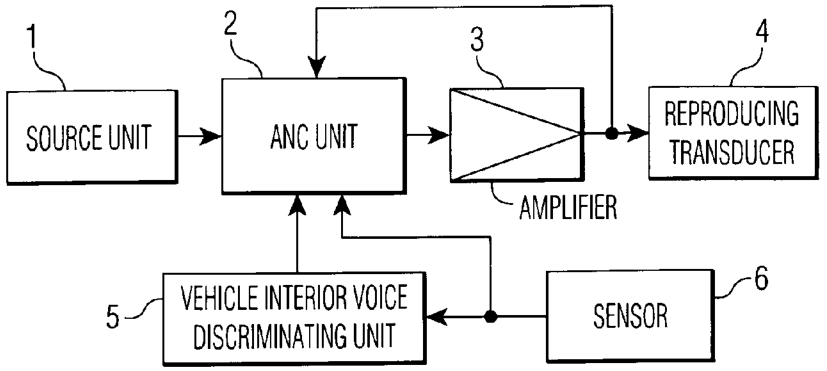
FIG. 1 is a block diagram for illustrating an exemplary embodiment of an active noise control system in accordance with the present invention.

FIG. 1 is a block diagram illustrating an exemplary embodiment of an active noise control system in accordance with the present invention. Signals emanating from source unit 1, such as a radio and compact disc (CD) are fed into ANC unit 2. The output of ANC unit 2 is fed into amplifier 3. The output of amplifier 3 is connected to reproducing transducer 4. The output of sensor 6 is fed into vehicle interior voice discriminating unit 5 and ANC unit 2, and the output of vehicle interior voice discriminating unit 5 is fed into ANC unit 2. The output of amplifier 3 is also fed into ANC unit 2.

In such a structure, its operation is described below.

Regenerative signals from source unit 1 are fed into ANC unit 2, where the signals are mixed with noise eliminating signals generated in the ANC unit, amplified by amplifier 3, and fed into such reproducing transducers 4 as speakers, so that the signals from source unit 1 are reproduced while noise is eliminated.

On the other hand, noise signals and various kinds of vehicle information signals transmitted from sensors 6 are fed into vehicle interior voice discriminating unit 5 and ANC unit 2. Such sensors include those comprising microphones for detecting information on the inside and outside of the vehicle and those for detecting the presence of passengers. Vehicle interior voice discriminating unit 5 discriminates the voices of passengers using the signals from sensors 6 and transmits ANC control signals to ANC unit 2 for switching ON/OFF the noise eliminating operation. ANC unit 2 generates noise elimination signals using the signals from sensors 6 and the output signals from amplifier 3, and the regenerative signals from source unit 1 and the noise elimination signals are mixed with the ANC control signals so as to form reproduced signals.

Figure 2:
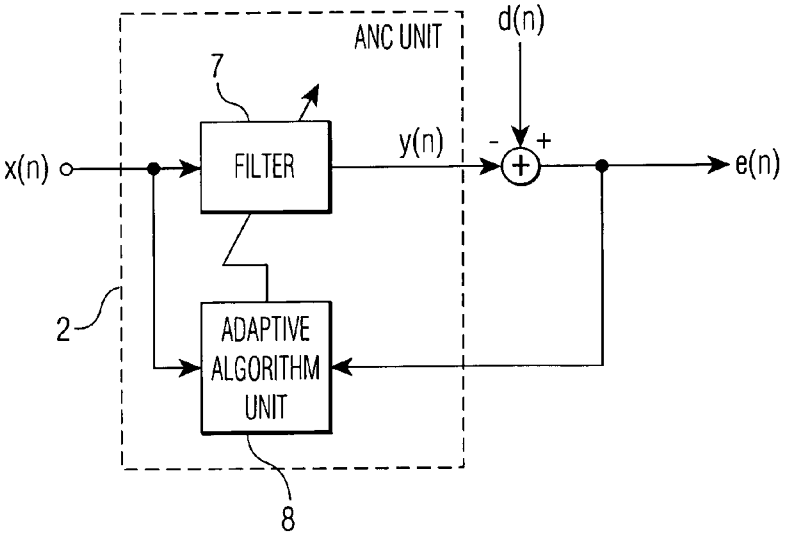
FIG. 2 is a block diagram for illustrating the basic operating principle of an ANC unit of the system.

FIG. 2 is a block diagram showing the basic structure of ANC unit 2. Noise reference signals x(n) that are obtained from some of sensors 6 are fed into filter 7 and adaptive algorithm unit 8. Output signals y(n) from filter 7 are subtracted from noise signals d(n) to be eliminated. The noise signals are also obtained from some of sensors 6. Resultant error signals e (n) are fed into adaptive algorithm unit 8.

Next, the noise elimination operation in ANC unit 2 is described. Noise reference signals x (n) are fed into filter 7 and output signals y (n), are supplied. Output signals y (n) are subtracted from noise signals d (n) and resultant error signals e (n) are obtained. Factors of filter 7 are sequentially updated by application of an adaptive algorithm, typified by the least-mean-square (LMS) algorithm, to these error signals e(n) and noise reference signals x(n) in adaptive algorithm unit 8. This operation minimizes error signals e(n) and consequently allows elimination of noise signals d(n).

Figure 3:
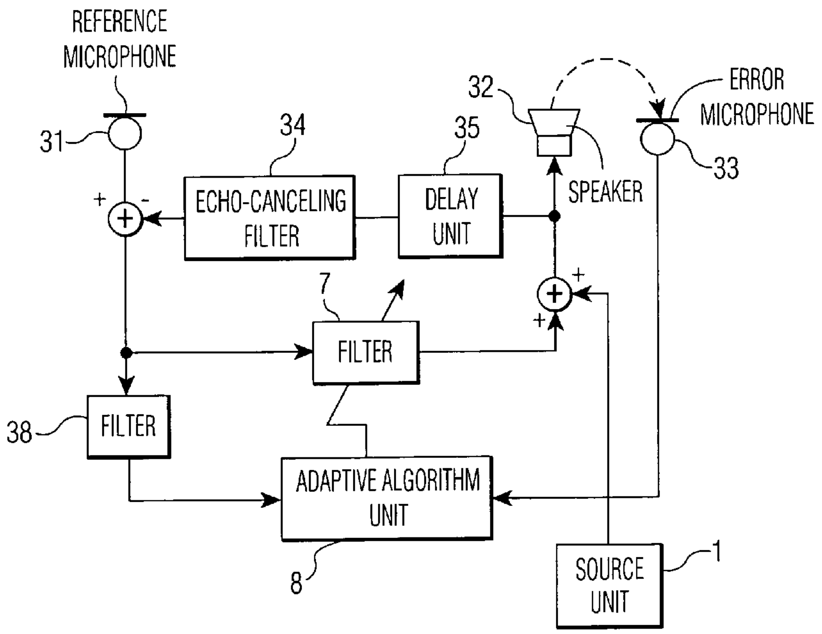
FIG. 3 is a block diagram for illustrating the noise eliminating operation of the system.

FIG. 3 is a block diagram for illustrating a specific noise elimination operation in the active noise control system shown in FIG. 1.

In FIG. 3, the same components as shown in FIGS. 1 and 2 are denoted with the same reference numerals. Detailed explanation of the same components is omitted and only the different components are detailed.

Signals transmitted from reference microphone 31 are fed into filters 7 and 38. The output of filter 7 is mixed with the signals from source unit 1 and supplied to speakers 32 as reproducing transducers 4 as well as delay unit 35. The output of delay unit 35 is fed into echo-canceling filter 34 and the output of the filter is subtracted from the signals from reference microphone 31. The output signals from filter 38 and error microphone 33 are fed into adaptive algorithm unit 8. The output of adaptive algorithm unit 8 is fed into filter 7.

Since output signals y(n) shown FIG. 2 undergo influence of a transfer function until they reach hearing points, filter 38 must be added to compensate such influence. Providing the filter compensates the influence the transfer function exerts on the sound transmitted from speaker 32 to error microphone 33.

Moreover, echo-canceling filter 34 is added in order to prevent the reproduced sound itself from being fed into as noise reference signals x(n). Delay unit 35 is provided to delay signals through echo-canceling filter 34 so that the signals coincide with the sound transmitted through the acoustic space because the signals through echo-canceling filter are transmitted via the electrical path. As a result, the sound fed from speaker 32 into reference microphone 31 is canceled out by the output of echo-canceling filter 34. Filter 38 and echo-canceling filter 34 are determined by system identification prior to the actual operation.

The signals from source unit 1 does not go through filter 7 and are added before reproduced output and thus do not undergo the filtering process for noise elimination. In addition, since echo-canceling filter 34 is effective, the signals from source unit 1 are not inversely affected and thus reproduced as they are together with noise elimination signals.

Figure 4:
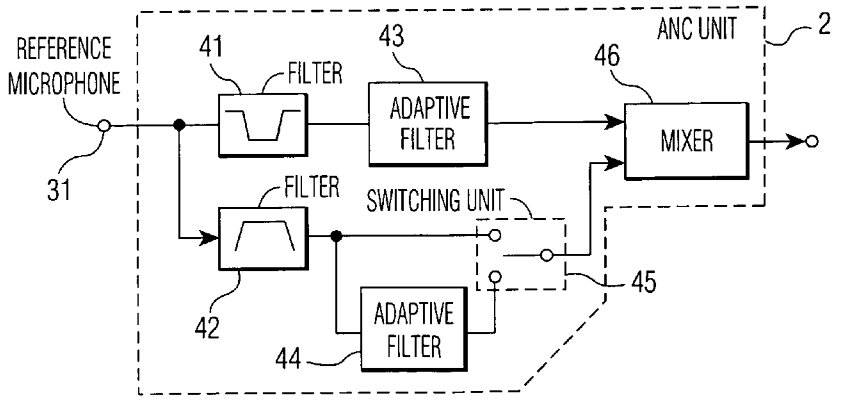
FIG. 4 is a block diagram for illustrating a detailed example of the ANC unit of the system.

FIG. 4 is a block diagram for illustrating a detailed example of ANC unit 2 as shown in FIG. 2.

The output signals from reference microphone 31, a kind of noise reference signals x(n), are connected to filters 41 and 42. The output of filter 41 is fed into adaptive filter 43 and the output of adaptive filter 43 is fed into mixer 46.

The output of filter 42 is connected to switching unit 45 and adaptive filter 44. The output of filter 44 is fed into switching unit 45 and the output of switching unit 45 is fed into mixer 46.

Filter 41 allows the signals outside of the voice band to go through. The signals outside of the voice band that have passed through filter 41 go into adaptive filter 43, where the noise outside of the voice band are adapted for elimination. Filter 42 allows signals within the voice band to go through. Signals that have passed through filter 42 go into adaptive filter 44, where the signals within the voice band are adapted for elimination. Responsive to the output signals from vehicle interior voice discriminating unit 5, switching unit 45 switches so as to select either the signals from filter 42 without adaptation or adapted signals. Then the selected signals are mixed in mixer 46 for output. As described above, when voice emanates in the vehicle interior, all the signals from filter 42 are used without adaptation; thus sound within the voice band, i.e. conversation, is not eliminated. Noise outside of the voice band, however, is eliminated.

The factors of adaptive filters 43 and 44 can be set arbitrarily by switching. They can be continuously updated or fixed.

Figure 5:
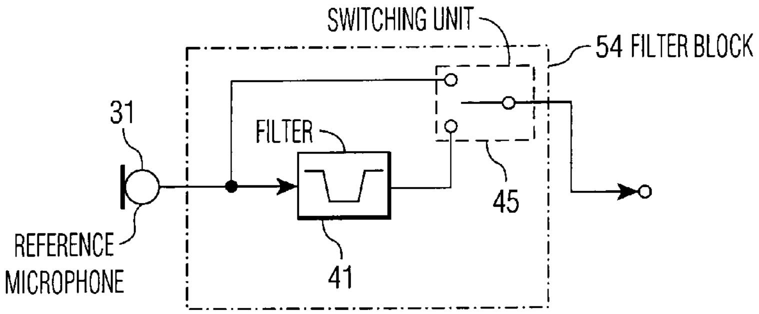
FIG. 5 is a block diagram for illustrating another example of the ANC unit of the system.

FIG. 5 is a block diagram for illustrating another example of ANC unit 2 shown in FIG. 2.

In FIG. 5, the same components as shown in FIGS. 2 and 4 are denoted with the same reference numerals. Detailed explanation of the same components is omitted and only the different components are detailed.

In FIG. 5, the signals from reference microphone 31 are fed into filter block 54. In block 54, the signals are fed into filter 41 and switching unit 45. The output of filter 41 is fed into switching unit 45.

The input signals (the output signals of reference microphone 31) are fed into filter 41 that allows the signals outside of the voice band to go through. Responsive to the output signals from vehicle interior voice discriminating unit 5, switching unit 45 switches so as to select either allowing passage of all the signals without filtration or filtering out using filter 41. Thus, this ANC unit stops the noise eliminating operation on the signals within the voice band (i.e. conversation) when voice has emanated in the vehicle interior.

Figure 6:
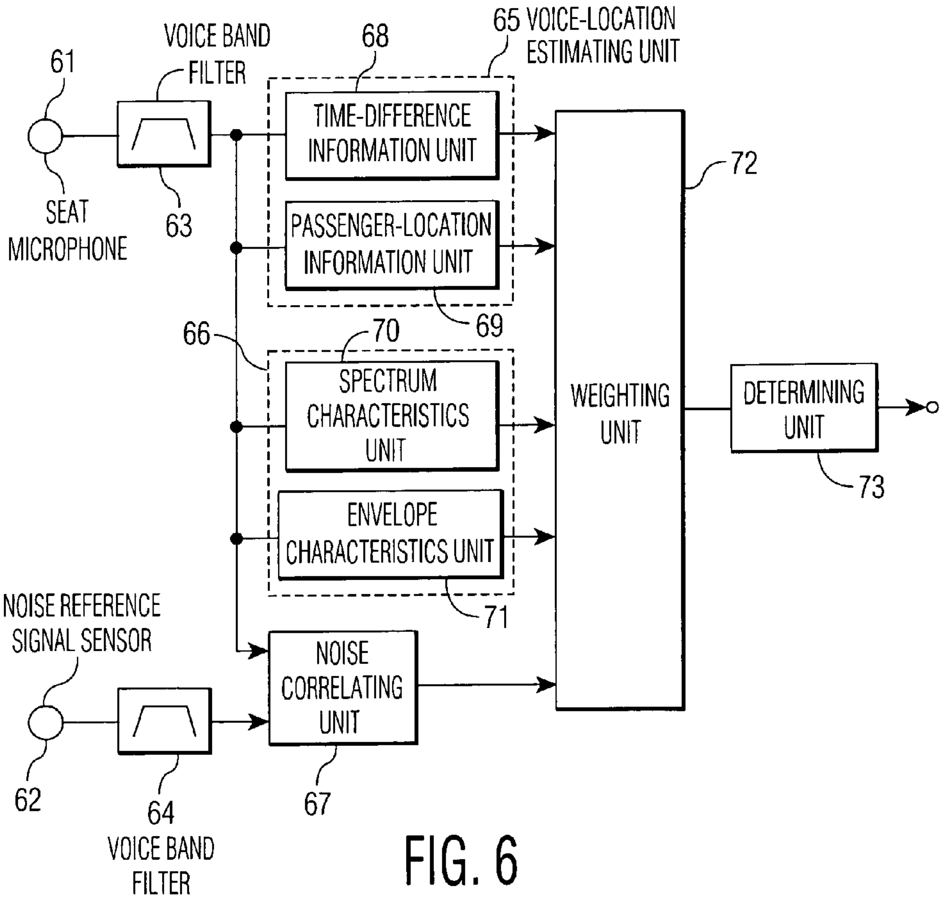
FIG. 6 is a block diagram for illustrating a vehicle interior voice discriminating unit of the system.

FIG. 6 is a block diagram for illustrating vehicle interior voice discriminating unit 5.

Signals from seat microphones 61, some of sensors 6, are fed into voice band filter 63. The output of filter 63 is fed into time-difference information unit 68 and passenger-location information unit 69 in voice-location estimating unit 65 and also fed into spectrum characteristics unit 70 and envelope characteristics unit 71 in voice-likelihood estimating unit 66. The output of filter 63 is also fed into noise correlating unit 67. The output of noise reference signal sensors 62 is fed into voice band filter 64. The output of voice band filter 64 is fed into noise correlating unit 67. The outputs of voice-location estimating unit 65, voice-likelihood estimating unit 66, and noise correlating unit 67 are fed into weighting unit 72, and the output of weighting unit 72 is fed into determining unit 73.

FIG. 6 is an example showing the structure of vehicle interior voice discriminating unit 5. The signals from seat microphones 61 provided in the proximity of the passengers are restricted to those within the voice band by voice band filter 63, and then the restricted signals are fed into voice-location estimating unit 65, voice-likelihood estimating unit 66, and noise correlating unit 67. The signals from noise reference signal sensors 62 are restricted to those within the voice band by voice band filter 64, and then the restricted signals are fed into noise correlating unit 67. Voice-location estimating unit 65 comprises time-difference information unit 68, passenger-location information unit 69, and other components. Voice-likelihood estimating unit 66 comprises spectrum characteristics unit 70, envelope characteristics unit 71, and other components. The output from each of these components is fed into weighting unit 72. Noise correlating unit 67 examines the correlation between the signals from seat microphones 61 that have passed through filter 63 and the signals from noise reference signal sensors 62 that have passed through voice band filter 64, and supplies the degree of correlation to weighting unit 72. Weighting unit 72 assigns weights to each input signal and supplies the sum of the weighted input to determining unit 73. The determining unit 73 supplies control signals according to preset threshold values.

Time-difference information unit 68 utilizes the order in which signals from seat microphones 61 emanate. Passenger-location information unit 69 utilizes the volume of the signals from seat microphones 61 and passenger-detecting sensors 78 (detailed in FIG. 7).

Figure 7:
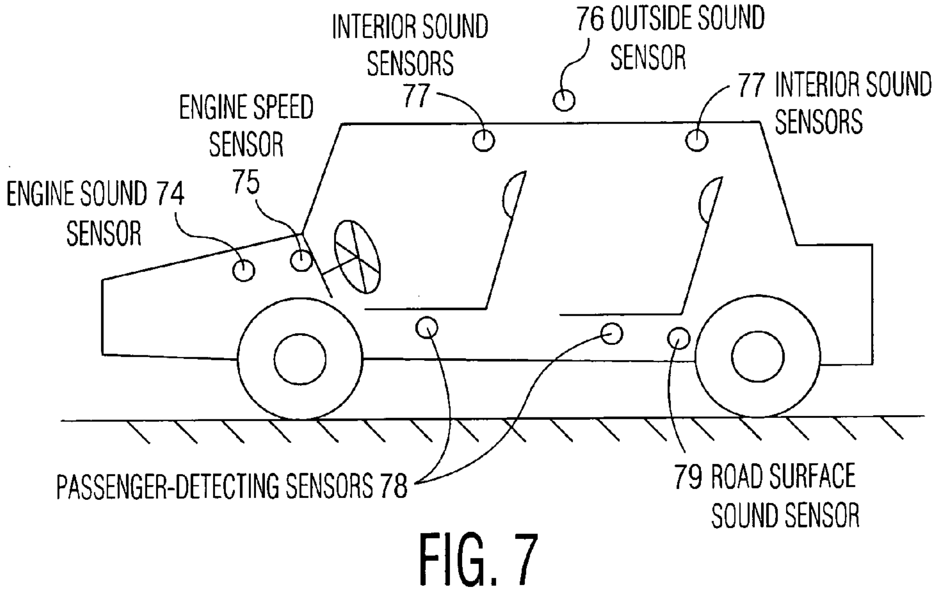
FIG. 7 is a layout diagram for illustrating an arrangement example of some of the sensors in the system.

FIG. 7 is a layout diagram for illustrating an arrangement example of some of sensors 6.

Provided in a bonnet are engine sound sensor 74 and engine speed sensor 75. Provided in a vehicle interior are interior sound sensors 77 on the ceiling and passenger-detecting sensors 78 under the seats. In addition, outside sound sensor 76 is provided from the ceiling to the outside and road surface sound sensor 79 is provided in the proximity to the tire house.

Figure 8:
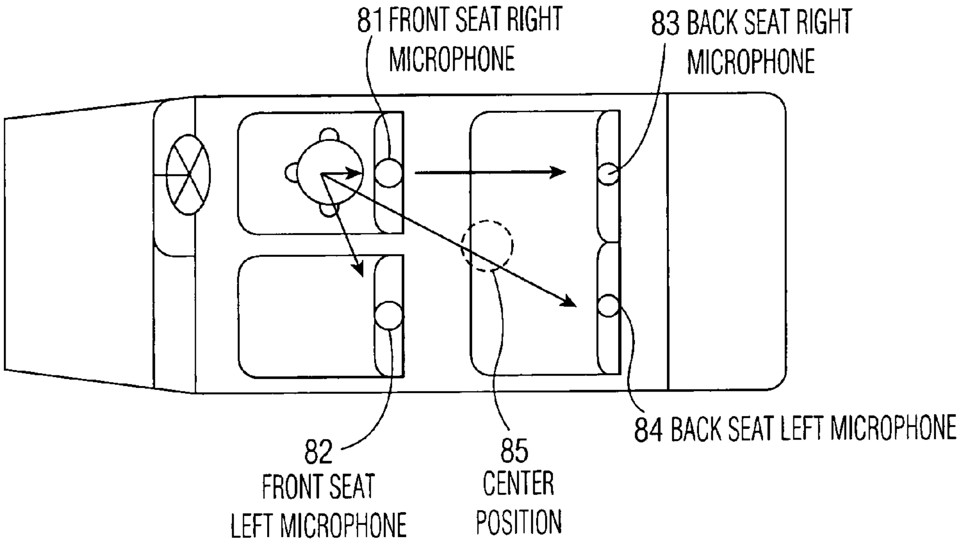
FIG. 8 is a layout diagram for illustrating an arrangement example of seat microphones of the system.

FIG. 8 is a layout diagram for illustrating an arrangement example of seat microphones 61.

The front seat right headrest is provided with front seat right microphone 81 and the front seat left headrest is provided with front seat left microphone 82. Similarly, the backseats are provided with backseat right microphone 83 and backseat left microphone 84. The point equidistant from the head position of each seat is shown by center position 85.

Vocal signals generated by a driver reach each of seat microphones 81 through 84 at different time. On the other hand, if the vocal signals emanate from central position 85 of the vehicle, they reach each microphone at the same time. Therefore, measuring the time difference among the signals emanating from each of seat microphones 81 through 84 allows estimation of the position at which voice has emanated. The estimation can be more accurate when the information from passenger-detecting sensors 78 is taken into account.

These concepts are used for time-difference information unit 68 and passenger-location information unit 69 shown in FIG. 6.

Sensors 6 include various types that are capable of detecting sounds and vibrations outside of the running vehicle, information on factors affecting the vehicle interior acoustic space, and such operating conditions as running speeds of the vehicle, other than the sensors described above.

The use of the information described in FIGS. 6 through 8 improves the accuracy in discrimination of the voice.

Figure 9A:
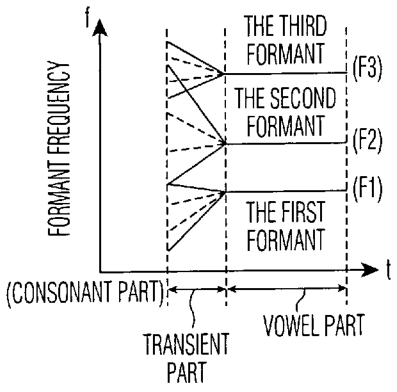
FIG. 9A is a transition diagram showing the formant frequencies of a phoneme varying with time in the vehicle interior voice discriminating unit of the system.
Figure 9B:
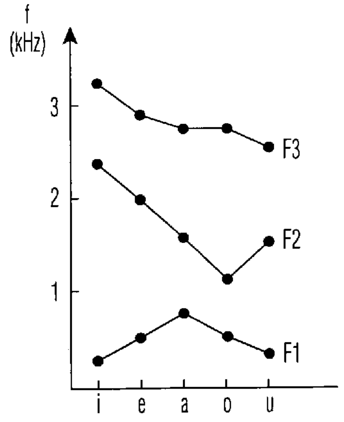
FIG. 9B is a schematic diagram for illustrating formant characteristics of the vowels in the vehicle interior voice discriminating unit of the system.

FIG. 9A is a transition diagram showing formant frequencies of a phoneme varying with time in vehicle voice discriminating unit 5 and FIG. 9B is a schematic drawing for illustrating the characteristics of the formants of the vowels.

FIG. 9A shows a typical pattern of a phoneme, indicating that a formant becomes stable after going through its consonant and transient parts and reaches its vowel part. FIG. 9B shows the formants of vowel parts. It is seen that each vowel has the first, second and third formants (F1, F2 and F3) different from each other. Therefore, such a pattern can be utilized for discrimination between noise and voice. In general, rotating sound of an engine and the like has a noise pattern that is an integral multiple. Such a sound as wind has a flat spectrum due to its random property and thus often has a pattern different from a voice pattern. If the noise patterns of the vehicle are understood in relation with its speed and engine speed, such known information can be also used for the discrimination.

Using these characteristics further improves the accuracy in discrimination of the voice.

Figure 10:
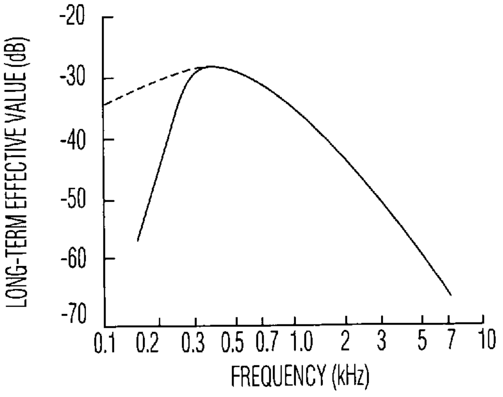
FIG. 10 is a graph for illustrating a long-term power spectrum effective value of the voices in the vehicle interior voice discriminating unit of the system.

FIG. 10 is a graph for illustrating a long-term power spectrum effective value of voices in vehicle interior voice discriminating unit 5. The solid line indicates a female voice and broken line indicates a male voice. Major power lies between 300 Hz and 1 kHz and the power considerably attenuates toward higher frequencies. Therefore, filters covering up to 2 to 3 kHz are sufficient. From the viewpoint of phonetics, filters covering up to the second formant are almost effective. In addition, since noise is somewhat more persistent than voice, such information on signal envelopes can also be used for the discrimination. These characteristics are used for spectrum characteristics unit 70 and envelope characteristics unit 71.

Figure 11:
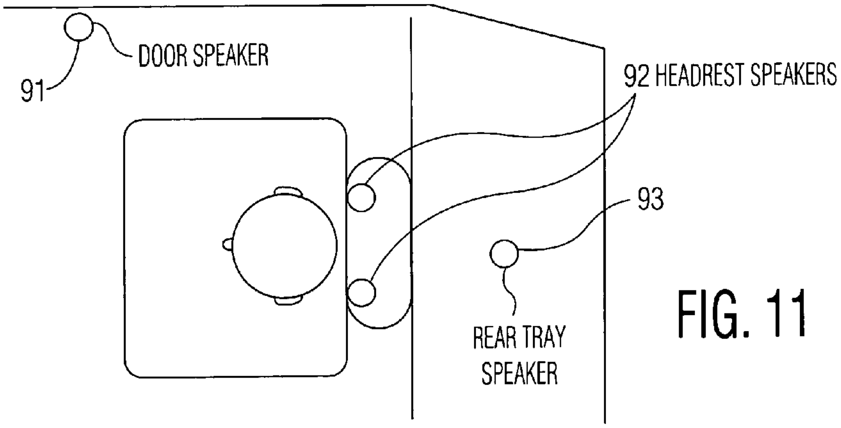
FIG. 11 is a layout diagram for illustrating an arrangement example of speakers of the system.

FIG. 11 is a layout diagram for illustrating an arrangement example of speakers used as reproducing transducers 4.

While the doors carry door speakers 91 and the rear tray carries rear tray speakers 93, the headrests carry headrest speakers 92 close to persons' ears.

Since headrest speakers 92 are closer to the ears, i.e. hearing points, than door speakers 91 and rear tray speakers 93, errors generated during the transmission of sound from speaker 32 to error microphone 33 as explained in FIG. 3 are reduced. This arrangement allows more accurate control and thus elimination of the noise extending to a higher voice-frequency band.

Figure 12:
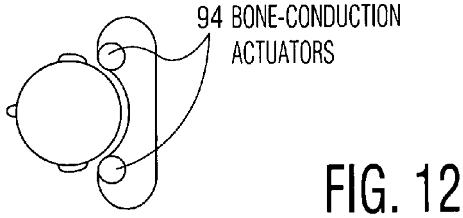
FIG. 12 is a layout diagram for illustrating an arrangement example of bone-conduction actuators of the system.

FIG. 12 is an arrangement diagram for illustrating an arrangement example of bone-conduction actuators as reproducing transducers 4.

The headrests carry bone-conduction actuators 94 close to the ears. Even for a voice frequency of 1 kHz, its half wave is about 15 cm, i.e. equivalent to the distance between both ears. Thus, for higher voice-frequency bands, speakers as the reproducing transducers are more difficult to be placed. Also from the viewpoints of the service area and interference with and by other speakers, bone-conduction actuators 94 are effective.

Figure 13:
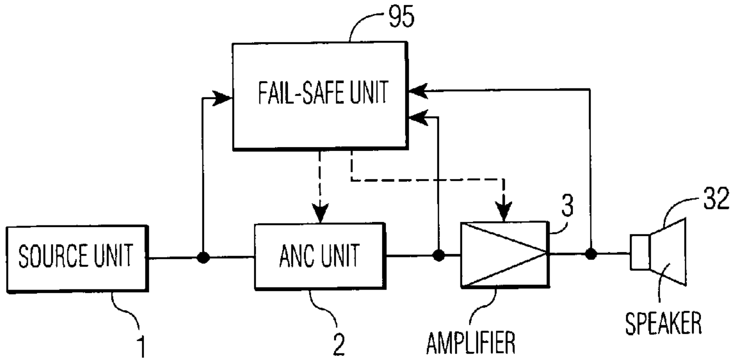
FIG. 13 is a block diagram for illustrating the operation of a fail-safe function of the system.

FIG. 13 is a block diagram for illustrating the operation of a fail-safe function in the active noise control system shown in FIG. 1.

In FIG. 13, the same components as shown in FIGS. 1 and 3 are denoted with the same reference numerals. Detailed explanation of the same components is omitted and only the different components are detailed.

The signals from source unit 1 are fed into fail-safe unit 95 and ANC unit 2. The output of ANC unit 2 is fed into amplifier 3 and fail-safe unit 95, and the output of amplifier 3 is fed into speaker 32 and fail-safe unit 95. The output of fail-safe unit 95 is fed into ANC unit 2 and amplifier 3.

The fail-safe function is structured so that fail-safe unit 95 receives the output signals from source unit 1, the output signals from ANC unit 2, and the output signals from amplifier 3, as monitoring signals, and then processed control signals (the output signals from fail-safe unit 95) control ANC unit 2 and amplifier 3. Specifically, the function controls processing signals (the output from fail-safe unit 95) so as to reduce the signals or restrict noise elimination operation when the signals become too large and distorted and give such an ill effect as impairing the noise elimination effect. When music source signals are too large for us to recognize the noise elimination effect, the function also controls to restrict noise elimination operation so that the reproduction dynamic range is not inversely affected.

INDUSTRIAL APPLICABILITY

As described above, the system of the present invention has: a source unit for generating regenerative signals; an ANC unit for processing signals so as to actively cancel noise; sensors for detecting the information on the inside and outside of a vehicle; a vehicle interior voice discriminating unit for discriminating voice of conversation generated in the vehicle interior; an amplifier for amplifying the signals processed by the ANC unit; and reproducing transducers for reproducing the signals amplified by this amplifier. This structure allows reduction of noises extending to medium- and high-frequency bands in the interior of a vehicle.

The invention claimed is:

1. An active noise control (ANC) system comprising:

a source unit for generating regenerative signals;

an ANC unit for processing signals so as to actively cancel noise;

sensors for detecting information on the inside and outside of a vehicle;

a vehicle interior voice discriminating unit for discriminating voice of conversation in the interior of the vehicle;

an amplifier for amplifying the signals processed by said ANC unit;

a reproducing transducer for reproducing the signals amplified by said amplifier;

a first filter for allowing the output signals outside of a voice band supplied from said sensors to go through;

a first adaptive filter for eliminating noises outside of the voice band from the output of said first filter;

a second filter for allowing the output signals within the voice band supplied from said sensors to go through;

a switching unit for switching operations so as to select one of allowing passage of all the output from said second filter without filtration when voice is present in said vehicle interior and allowing the output from said second filter to pass through a second adaptive filter for eliminating noises within the voice band when no voice is present in said vehicle interior; and a mixer for mixing the output from said first adaptive filter and the output from said switching unit, wherein said ANC unit is structured so as to change processing effect thereof on noise in the voice band according to control signals supplied from said vehicle interior voice discriminating unit.

2. The active noise control system as described in claim 1 wherein factors of said first and second adaptive filters are arbitrarily set by switching so as to be continuously updated and fixed.

3. The active noise control system as described in claim 1 wherein said ANC unit has a fail-safe unit for stopping noise reduction operation when the operation is ineffective.

4. The active noise control system as described in claim 3 wherein said fail-safe unit also operates when the signals from said source unit are in a higher level.

5. An active noise control (ANC) system comprising:

a source unit for generating regenerative signals;

an ANC unit for processing signals so as to actively cancel noise;

sensors for detecting information on the inside and outside of a vehicle;

a vehicle interior voice discriminating unit for discriminating voice of conversation in the interior of the vehicle;

an amplifier for amplifying the signals processed by said ANC unit;

a reproducing transducer for reproducing the signals amplified by said amplifier;

wherein said sensors include a type for detecting information on factors affecting the acoustic space of the vehicle including the number of passengers and the location thereof, a type for detecting operating conditions of the vehicle, and one of a type for-detecting vehicle interior sounds, engine sound, and sounds and vibrations outside of the running vehicle;

wherein said sensors for detecting the location of passengers are arranged in predetermined positions and the number of sensors are such that generated voice is located; and, wherein said sensors for detecting the location of passengers are microphones placed in the vicinity of the heads of passengers.

6. The active noise control system of claim 5, wherein said operating conditions include engine speeds and running speeds.

* * * * *